(12) United States Patent
Kelland et al.

(10) Patent No.: US 8,540,082 B2
(45) Date of Patent: Sep. 24, 2013

(54) CENTRIFUGAL ASSEMBLY AND METHOD FOR OVA DETECTION

(75) Inventors: James Kelland, E. Walpole, MA (US); Henry Petithory, Southborough, MA (US); Kevin Sullivan, Chestnut Hill, MA (US)

(73) Assignee: Iris International, Inc., Chatsworth, CA (US)

( * ) Notice: Subject to any disclaimer, the term of this patent is extended or adjusted under 35 U.S.C. 154(b) by 348 days.

(21) Appl. No.: 13/120,984

(22) PCT Filed: Sep. 25, 2009

(86) PCT No.: PCT/US2009/058384
§ 371 (c)(1),
(2), (4) Date: Mar. 25, 2011

(87) PCT Pub. No.: WO2010/036895
PCT Pub. Date: Apr. 1, 2010

(65) Prior Publication Data
US 2011/0177931 A1    Jul. 21, 2011

Related U.S. Application Data

(60) Provisional application No. 61/194,456, filed on Sep. 26, 2008.

(51) Int. Cl.
*B04B 5/02* (2006.01)
*B04B 7/00* (2006.01)

(52) U.S. Cl.
USPC ............... 210/516; 210/515; 494/17; 422/72; 422/401; 422/533; 209/17; 209/173

(58) Field of Classification Search
USPC ............. 494/17; 422/72, 401, 533; 210/515, 210/516; 209/17, 173
See application file for complete search history.

(56) References Cited

U.S. PATENT DOCUMENTS

| | | | |
|---|---|---|---|
| 4,144,983 A | 3/1979 | Pauls et al. |
| 4,288,316 A | 9/1981 | Hennessy |
| 4,293,405 A | 10/1981 | Greenwald |
| 4,318,803 A | 3/1982 | Holmgren |
| 4,678,559 A | 7/1987 | Szabados |
| 4,771,297 A | 9/1988 | Lecheheb et al. |
| 4,859,610 A | 8/1989 | Maggio |
| 4,990,253 A | 2/1991 | Vcelka |
| 5,853,093 A | 12/1998 | Neiger |
| 6,063,038 A | 5/2000 | Diamond et al. |
| 2006/0115385 A1 | 6/2006 | Jon Meyer et al. |
| 2007/0299363 A1 | 12/2007 | Wong |

* cited by examiner

FOREIGN PATENT DOCUMENTS
WO    WO 2010036895 A1 *  4/2010

OTHER PUBLICATIONS

International Preliminary Report on Patentability for PCT/US2009/058384, dated Mar. 2011.*

Primary Examiner — David A Reifsnyder
(74) Attorney, Agent, or Firm — Preti Flaherty Beliveau & Pachios LLP

(57) ABSTRACT

A centrifugal assembly is provided that can be used in common laboratory fixed angle or swinging bucket centrifuges for the separation of material, such as parasitic ova, based on particle density. The centrifugal assembly allows the fluid level to be gently adjusted to form a meniscus without disruption of the buoyant matter, such as ova. The centrifugal assembly also enables a user to easily and hygienically collect and transfer a measured amount of a sample, such as fecal material, and to break apart and mix the sample with a floatation fluid contained in a centrifuge tube.

14 Claims, 16 Drawing Sheets

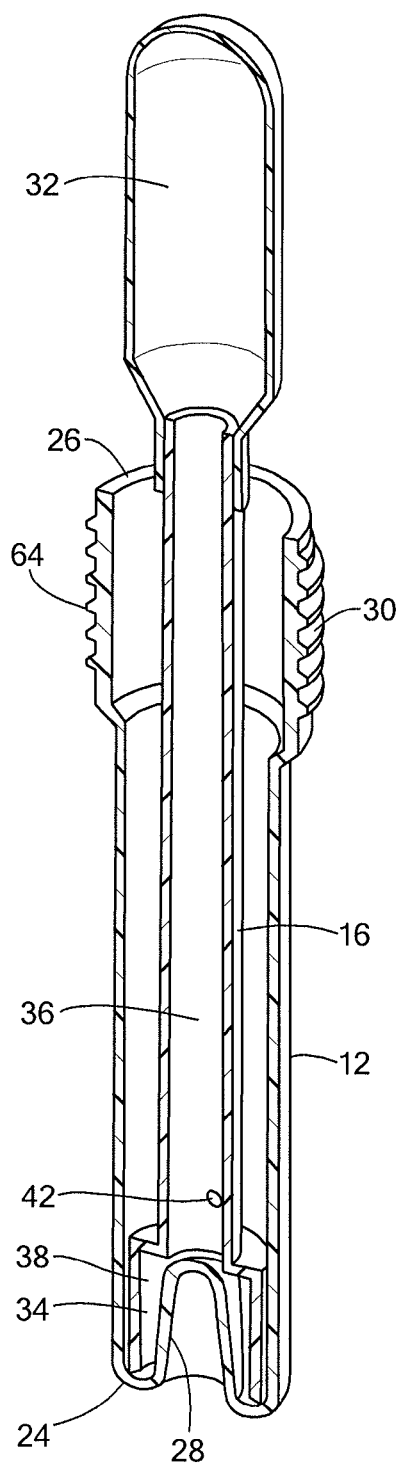
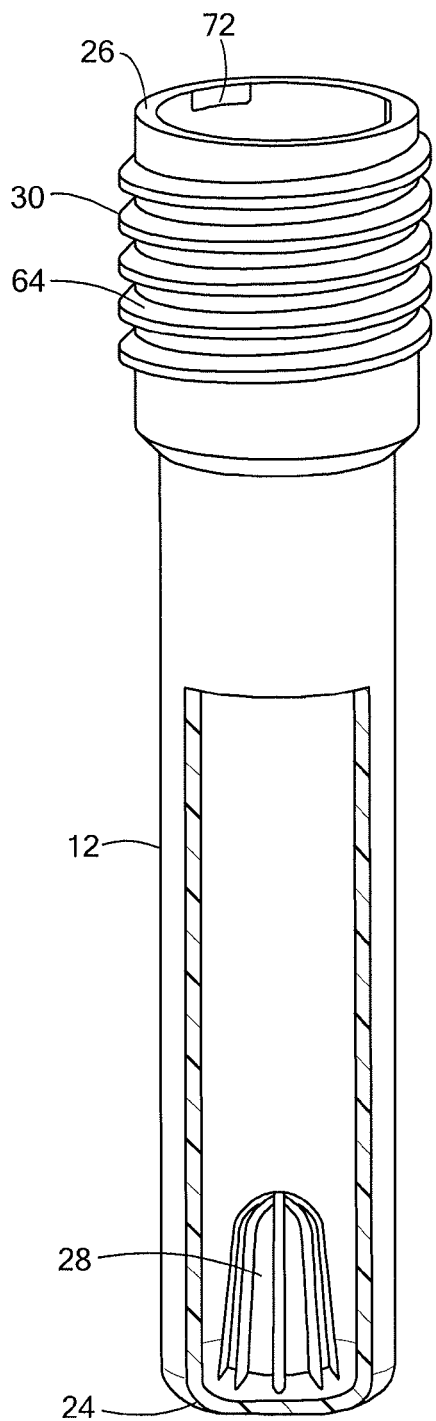
FIG. 1
FIG. 2

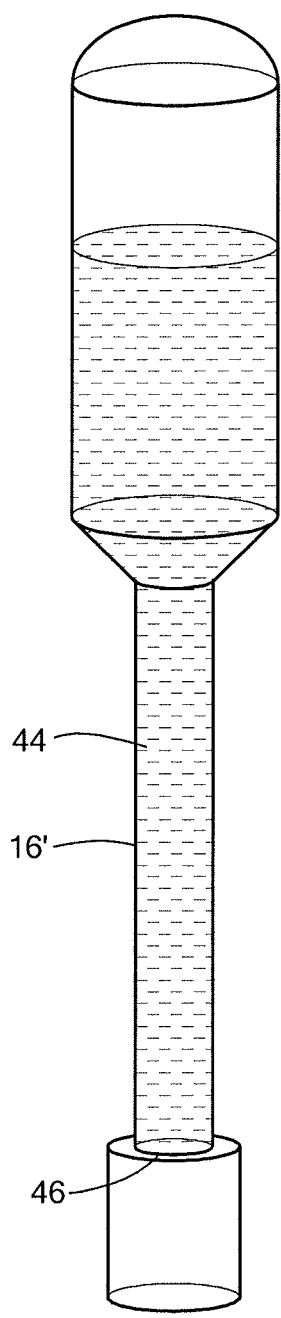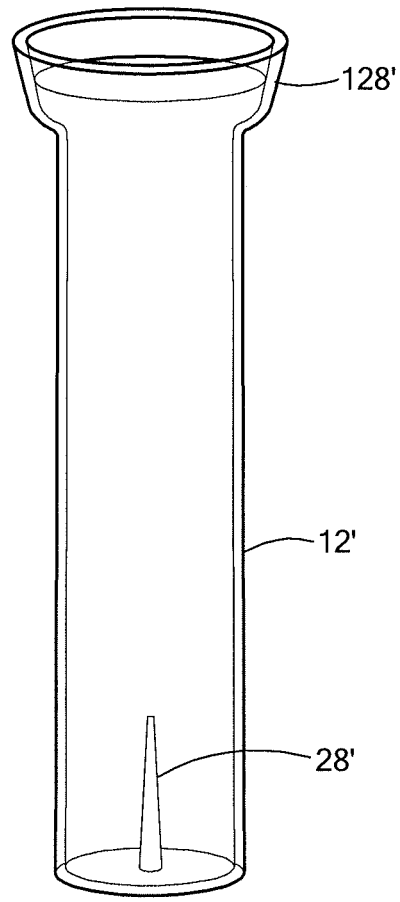
*FIG. 10*
*FIG. 9*

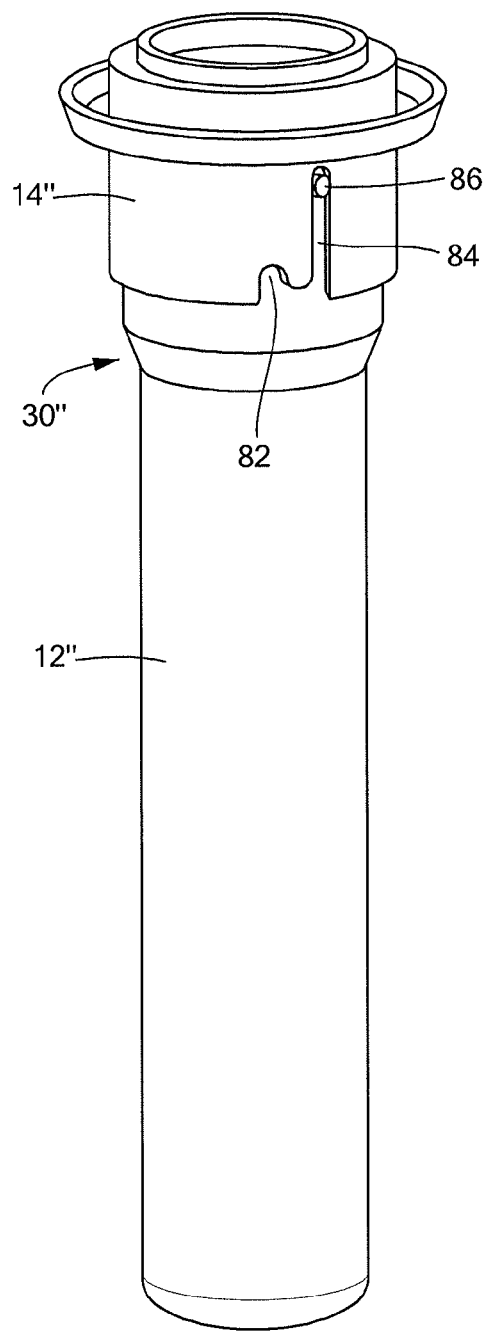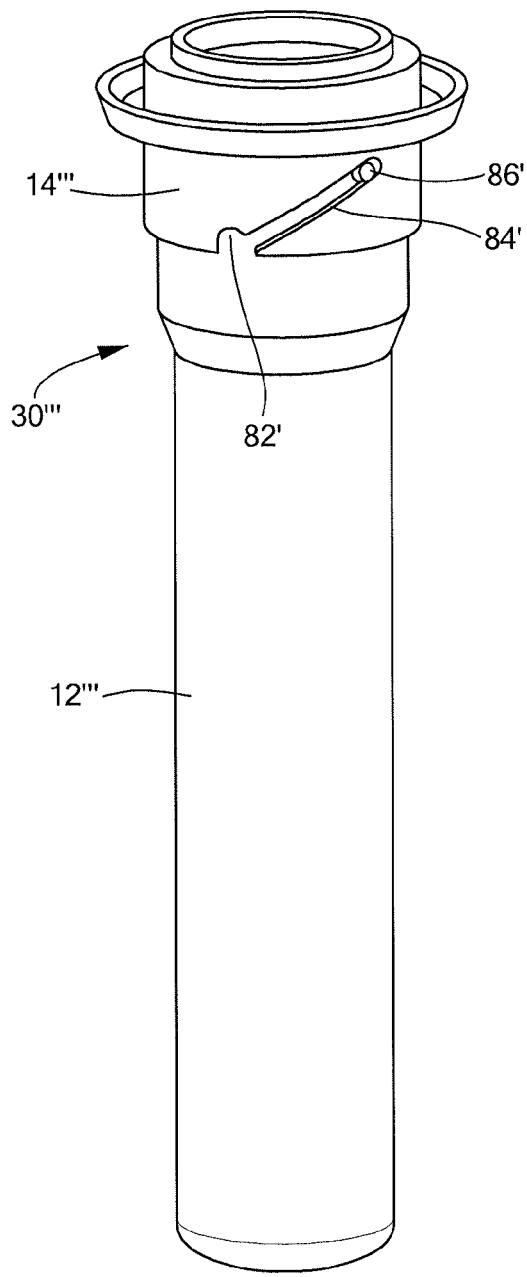
FIG. 11
FIG. 12

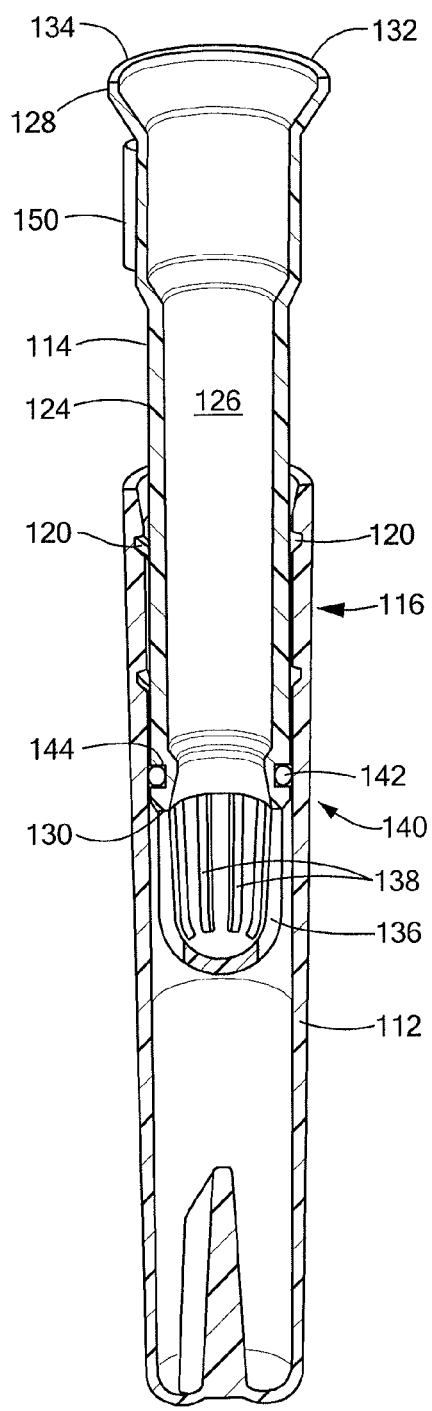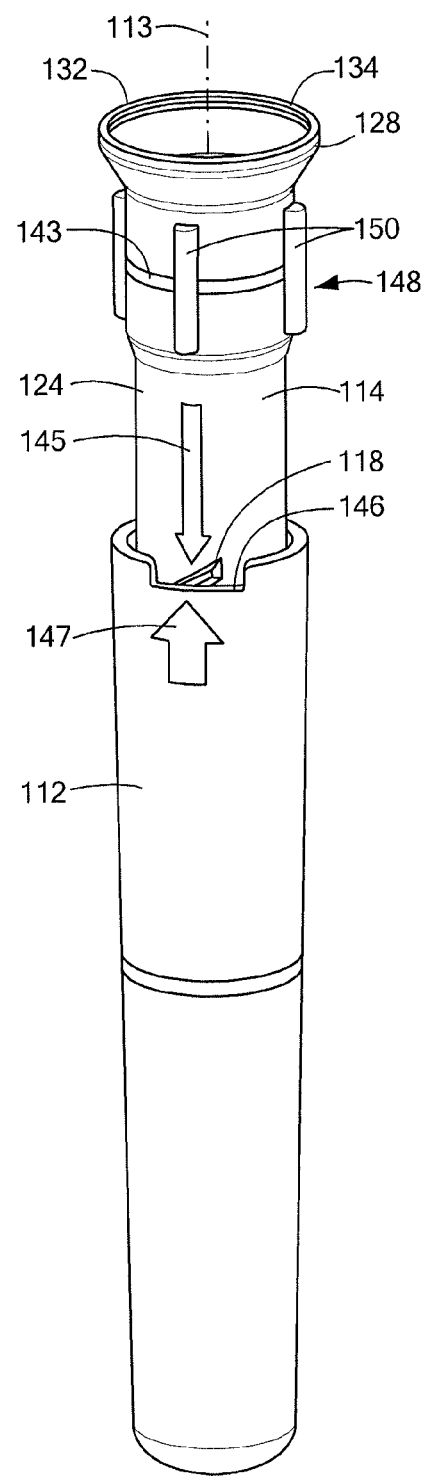
*FIG. 15*  *FIG. 16*

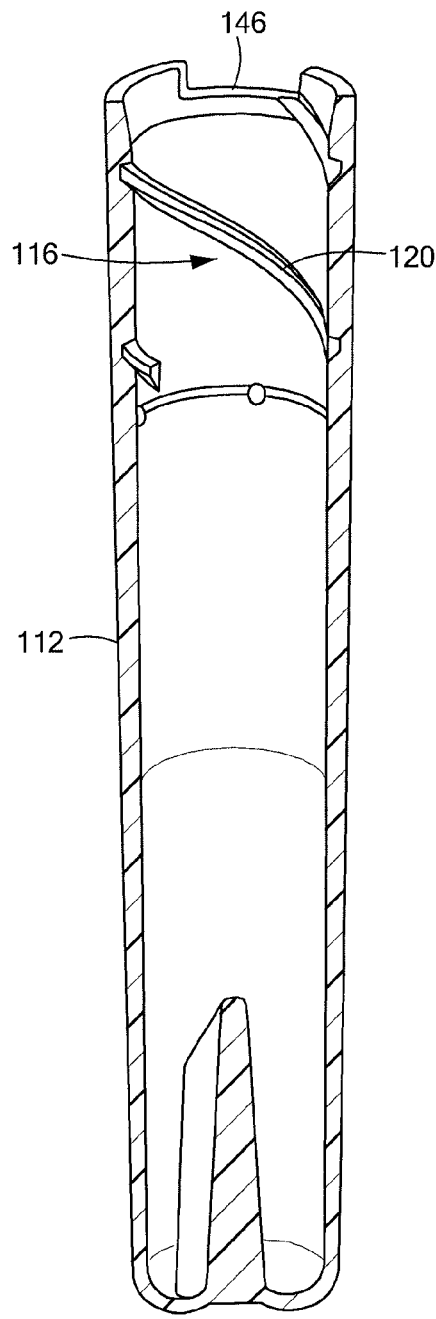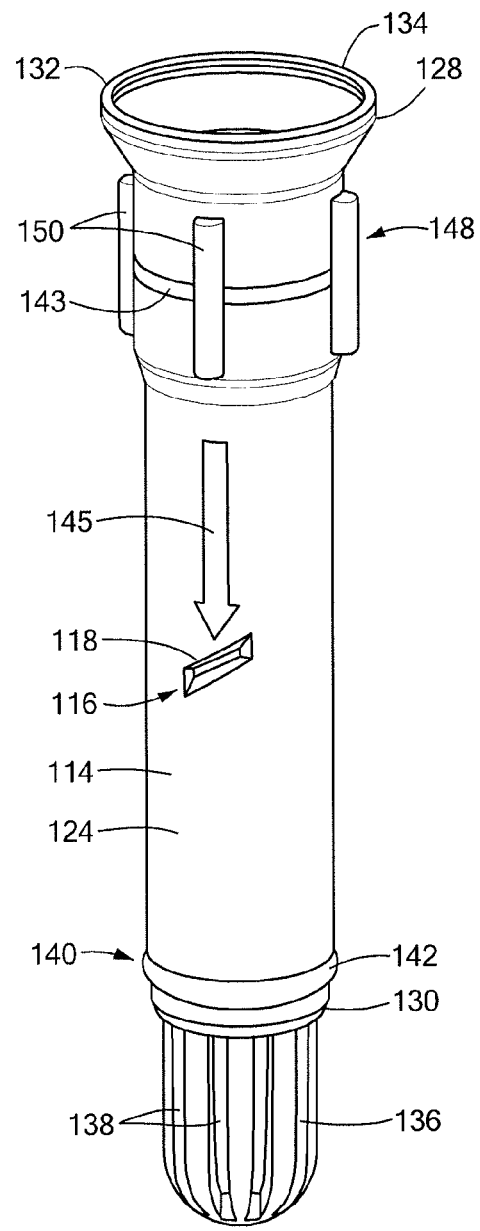
*FIG. 17*     *FIG. 18*

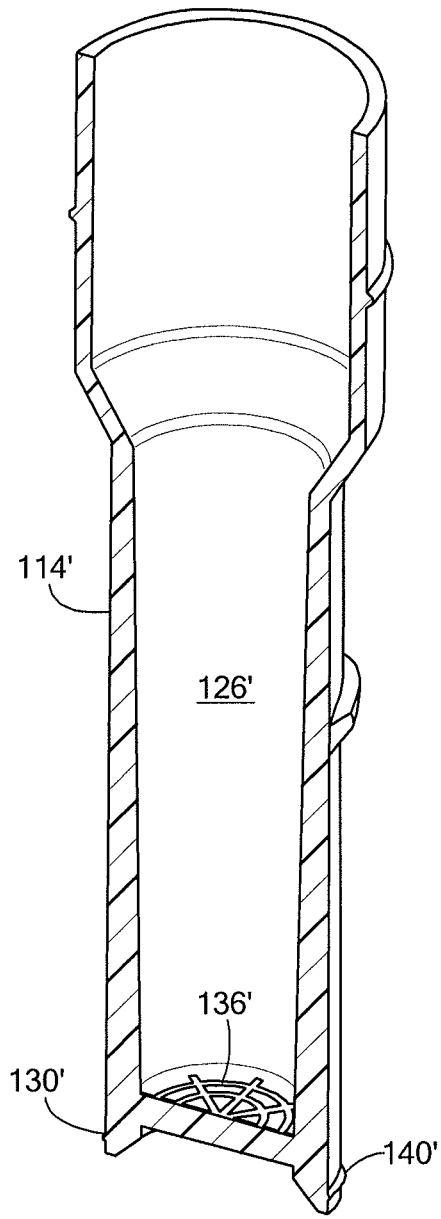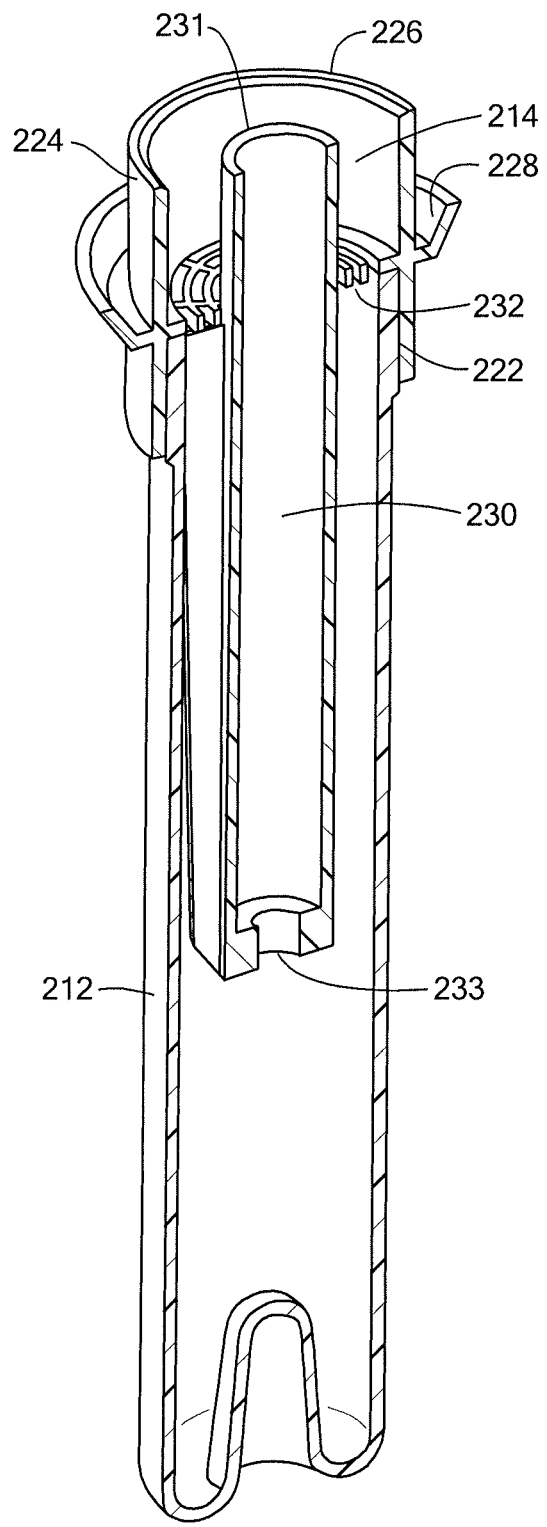
*FIG. 18A*
*FIG. 19*

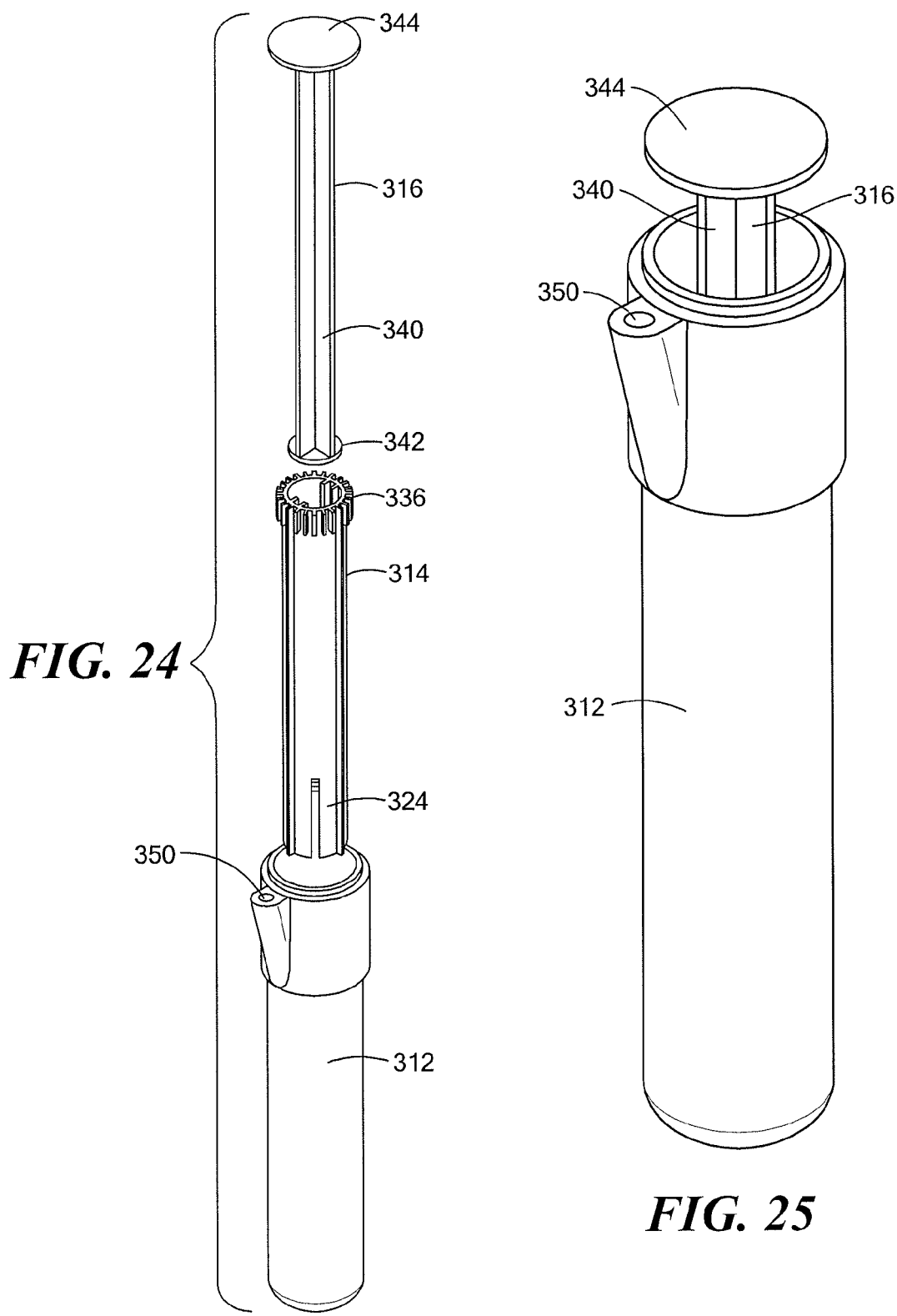

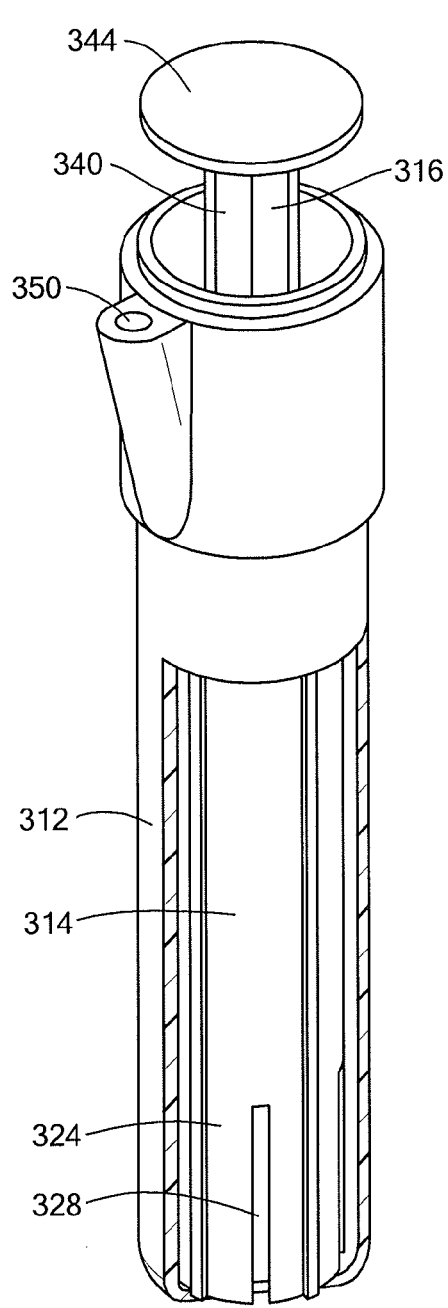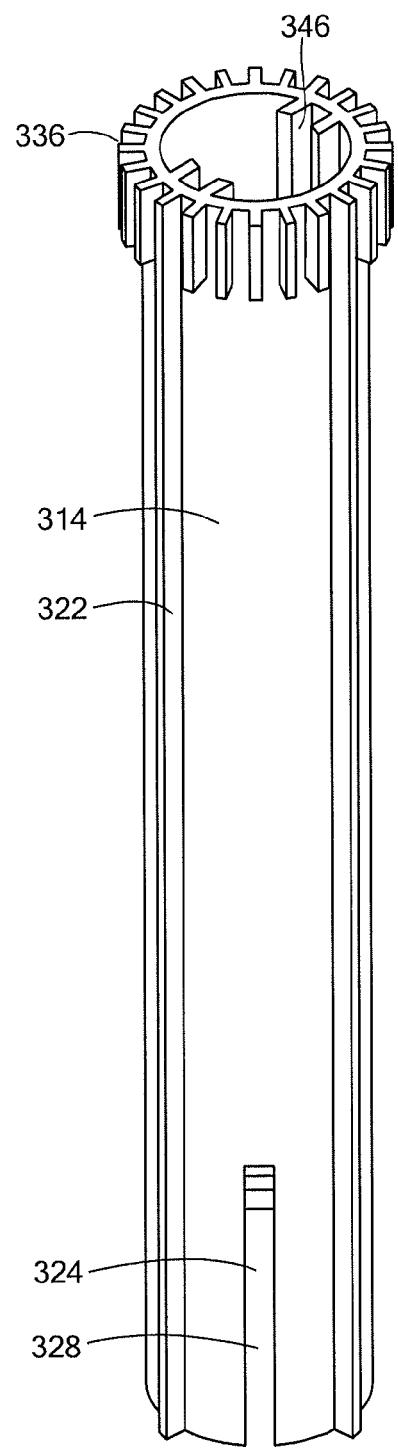
*FIG. 26*
*FIG. 27*

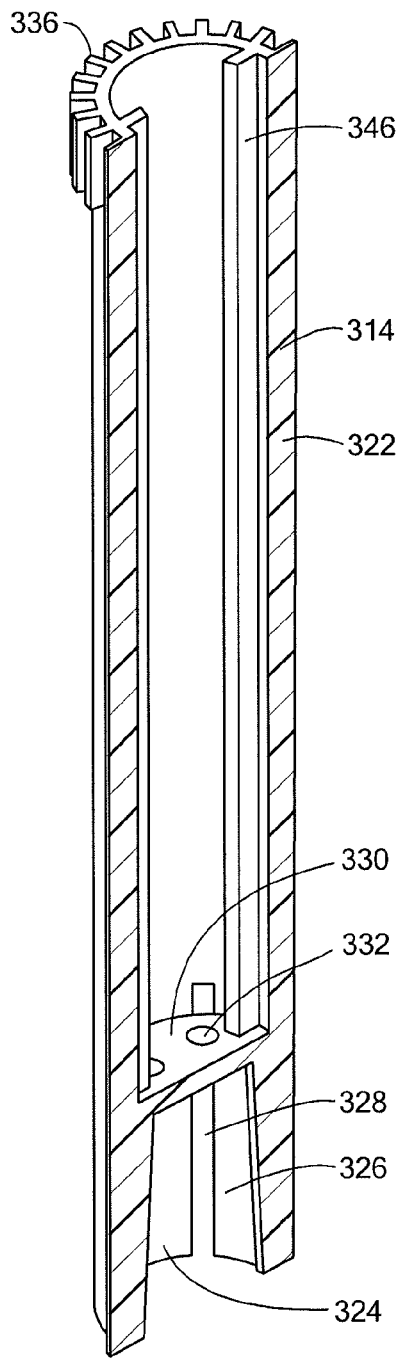
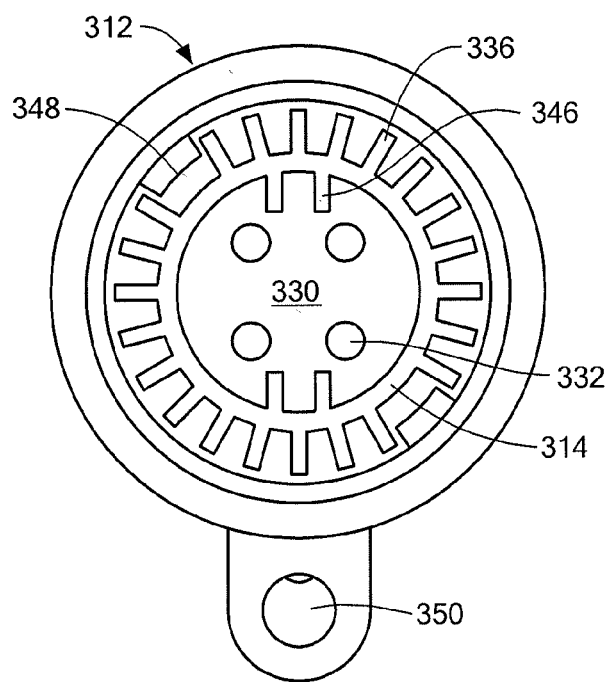
*FIG. 28*
*FIG. 29*

CENTRIFUGAL ASSEMBLY AND METHOD FOR OVA DETECTION

CROSS REFERENCE TO RELATED APPLICATIONS

This application claims the benefit under 35 U.S.C. §119(e) of U.S. Provisional Application No. 61/194,456, filed Sep. 26, 2008, the disclosure of which is incorporated by reference herein.

STATEMENT REGARDING FEDERALLY SPONSORED RESEARCH OR DEVELOPMENT

N/A

BACKGROUND OF THE INVENTION

It has long been recognized that analyzing fecal specimens for parasite ova by microscopy is a simple and effective method for identifying parasites afflicting a patient. This method is routinely used in clinical and veterinary laboratories around the world to identify specific parasites in fecal specimens from animals and humans so that the patient may be properly treated for the affliction.

There are a variety of laboratory techniques in common use to detect the presence of ova in a fecal sample. The simplest of these is the direct smear technique in which a small sample of patient feces is mixed with saline and "smeared" across the surface of a microscope slide. A coverslip is placed over the smear and the specimen is examined microscopically for parasite ova. This technique is rarely used in modern laboratories because the presence of debris in the fecal sample makes direct examination extremely difficult and prone to error. Also, the small sample size used makes it likely that a low population of parasites, such as during the early stages of an infestation, may not be detected.

For many years the preferred technique, in several variations, has been the use of a float-or-sink process in which a reagent liquid of a density between that of the ova and that of fecal matter is vigorously mixed into the fecal specimen to allow ova contained within the feces to be released to the liquid, and the ova then allowed to separate by floatation from the fecal debris. The ova, having floated to the top of the liquid, are then transferred to a microscope slide, such as by touching a coverslip to the surface of the liquid and placing the coverslip onto a microscope slide. Under the microscope, the type of ova and therefore the specific parasites present in the sample can be identified, and the seriousness of the infestation can be determined by counting and recording the number of each type of ova. This prior art process has been improved over the years, but still is not optimized and suffers from several limitations including the risk of exposure of laboratory personnel to potentially dangerous pathogens, complexity, unpleasant odor and also a degree of unreliability or inaccuracy.

Early improvements to this procedure were a) the prefiltration of the feces and floatation mixture, typically through a strainer, to remove clumps and undigested vegetable matter which may be contained in the fecal specimen and which would float to the surface of the liquid along with the ova, and b) the centrifugation of the prefiltered mixture to accelerate the process and provide a sharper separation of ova and fecal debris. While this latter technique proved to be more accurate and reliable, the multiple transfer steps involved and the high potential for spills and aerosol generation limited the acceptance of the technique as a routine laboratory procedure.

From the 1970s onward, a number of low-cost stand-alone devices were introduced which combined sample collection, filtration of debris, and ova collection in a single disposable unit. The first of these devices, called the FECALYZER, consists of a container and a combination sample collection and straining part. In operation, the container is filled with a floatation reagent, the sample collector and strainer is used to collect a measured amount of feces and to effect mixing of the sample and floatation liquid in the container to release ova from the fecal sample and to allow passage of the ova through the integral strainer while retaining vegetable matter and other fecal debris in the lower portion of the device. A coverslip is placed upon the opening of the device at the liquid surface to receive the floating ova. While the FECALYZER and other similar devices such as the OVASSAY are widely used today, particularly in companion animal veterinary practices, the devices of this technique have several key deficiencies including a) the time required for complete floatation of ova to the surface of the liquid can be excessive thereby making it impossible to provide a diagnosis during a typical one-half hour patient appointment and b) without the benefit of prefiltration or pre-separation by centrifugation, the straining method of these devices under natural gravity may trap a portion of the ova thereby contributing to inaccuracy of the diagnosis.

The accuracy and sensitivity of veterinary fecal exams have recently come under close scrutiny because many common parasites found in companion animals can be transmitted from pets to owners. As a result, a number of professional veterinary societies have studied the accuracy and repeatability of various techniques for fecal parasite analysis and have universally concluded that only the centrifugal floatation method can produce the accuracy and sensitivity necessary to protect both pets and their owners and that the widely-used FECALYZER and similar devices are suboptimal for the procedure.

In the standard method for centrifugal floatation using a swinging bucket type laboratory centrifuge device, the fecal sample is placed in a tube, the tube is filled with a floatation fluid to form a meniscus, and a cover slip placed on top of the tube. Care is taken to avoid the trapping of air bubbles between the fluid and the underside of the coverslip. The tube is placed in a swinging bucket centrifuge and spun for an appropriate time, about ten minutes, during which fecal matter and debris that have a higher density than the floatation fluid are forced to the bottom of the tube, while the buoyant ova are forced to the surface of the fluid and adhere to the coverslip. After the spin cycle, the coverslip is removed and transferred to a microscope slide for analysis using standard microscopic methods. This centrifugal method has several drawbacks. First, swinging bucket centrifuges are costly and large, and are rarely found in veterinary laboratories and other environments where fecal floatations are performed. Moreover, the tube is subject to spillover when it is filled with the floatation fluid to form a meniscus. Also, the coverslip can be flung off if the centrifuge rotor accelerates or decelerates at a high rate.

In the standard method for centrifugal floatation using a fixed angle type centrifuge, of the kind commonly found in clinics and veterinary laboratories, the tube is restrained at an acute angle with respect to the vertical axis of rotation. Thus, the tube cannot be filled to the top to form a meniscus prior to centrifugation, and consequently a coverslip cannot be placed on the tube before the centrifugation step. The meniscus must be formed by adding fluid to the tube after centrifugation, which disturbs the ova floating on the surface. The tube must rest for about ten minutes after the fluid addition to allow the ova to ascend to the fluid surface and adhere to the coverslip.

SUMMARY OF THE INVENTION

A centrifugal assembly is provided that can be used in common laboratory fixed angle or swinging bucket centrifuges for the separation of material, such as parasitic ova, based on particle density. In one aspect, the centrifugal assembly addresses problems with forming a meniscus that are present in prior art devices. In another aspect, the centrifugal assembly enables a user to easily and hygienically collect and transfer a measured amount of a sample, such as fecal material, and break apart and mix the sample with a floatation fluid contained in a centrifuge tube.

In one embodiment, a centrifugal assembly for separation of buoyant material comprises a tube configured for containing a floatation fluid and a sample of matter to be separated. The tube is elongated with respect to an axis and includes an open upper end and a closed lower end. A meniscus-forming device is engageable with and movable along the tube with respect to the axis. The device comprises an insert configured for sealing engagement with an interior surface of the tube. The insert includes an interior region and an open upper end at which a meniscus is formable, and a filter element disposed to prevent passage of material of a size greater than openings in the filter element into at least a portion of the interior region of the sleeve.

In another embodiment, a centrifugal assembly for separation of buoyant material comprises a tube configured for containing a floatation fluid and a sample of matter to be separated. The tube is elongated and includes an open upper end and a closed lower end. A mixing post is formed at the closed lower end of the tube. A collector/mixer device comprises a coring chamber, a squeezable member, and a hollow stem connecting the coring chamber and the squeezable member to allow fluid flow to and from the coring chamber upon squeezing of the squeezable member. The collector/mixer device is configured to fit within the tube, and the coring chamber is configured to fit over the mixing post at the bottom of the tube.

In a further embodiment, a centrifugal assembly for separation of buoyant material comprises a tube configured for containing a floatation fluid and a sample of matter to be separated. The tube is elongated and includes an open upper end, a closed lower end, and a mixing post formed at the closed lower end of the tube. A mixer insert comprises a hollow cylindrical member, and a coring chamber is disposed at a lower end of the cylindrical member. The mixer insert is configured to fit within the tube, and the coring chamber is configured to fit over the mixing post at the bottom of the tube. A plunger comprising an elongated member is configured to fit within the hollow cylindrical member of the mixer insert. The plunger is reciprocable and rotatable within the tube to mix the sample of matter in the floatation fluid.

In yet another embodiment, a centrifugal assembly for separation of buoyant material comprises a tube configured for containing a floatation fluid and a sample of matter to be separated. The tube is elongated and includes an open upper end and a closed lower end. A meniscus-forming device comprising an insert is sealingly attached to the tube. The insert includes an upstanding collar including an open upper end at which a meniscus is formable, and a fill conduit open at each end and disposed within the collar and extending into the tube. An upper edge of the fill conduit is disposed below the upper end of the collar.

DESCRIPTION OF THE DRAWINGS

The invention will be more fully understood from the following detailed description taken in conjunction with the accompanying drawings in which:

FIG. 1 is a cross sectional isometric view of a tube and collector/mixer device of a centrifugal assembly according to the present invention;

FIG. 2 is a partially cut away view of the tube of FIG. 1;

FIG. 9 is a further embodiment of a collector/mixer device with floatation fluid sealed therein;

FIG. 10 is a further embodiment of a tube with integral overflow rim;

FIG. 11 is an isometric view of a further embodiment of a tube and cap with a detent and slot engagement mechanism;

FIG. 12 is an isometric view of a further embodiment of a tube and cap with a detent and angled slot engagement mechanism;

FIG. 15 is a cross-sectional isometric view of a further embodiment of a tube and insert according to the present invention;

FIG. 16 is an isometric view of the tube and insert of FIG. 15;

FIG. 17 is a cross-sectional isometric view of the insert of FIG. 15;

FIG. 18 is a cross-sectional isometric view of the tube of FIG. 15;

FIG. 18A is a cross-sectional isometric view of a further embodiment of an insert;

FIG. 19 is a cross-sectional isometric view of a still further embodiment of a tube and insert according to the present invention;

FIG. 24 is an exploded isometric view of a still further embodiment of the present invention including a tube, mixer insert, and plunger;

FIG. 25 is an isometric view of the tube and plunger of FIG. 24;

FIG. 26 is a partially cut away view of the tube, mixer insert, and plunger of FIG. 24;

FIG. 27 is an isometric device of the mixer insert of FIG. 24;

FIG. 28 is a cross-sectional isometric view of the mixer insert of FIG. 24; and

FIG. 29 is a top plan view of the tube and mixer insert of FIG. 24.

DETAILED DESCRIPTION OF THE INVENTION

Figure 7:
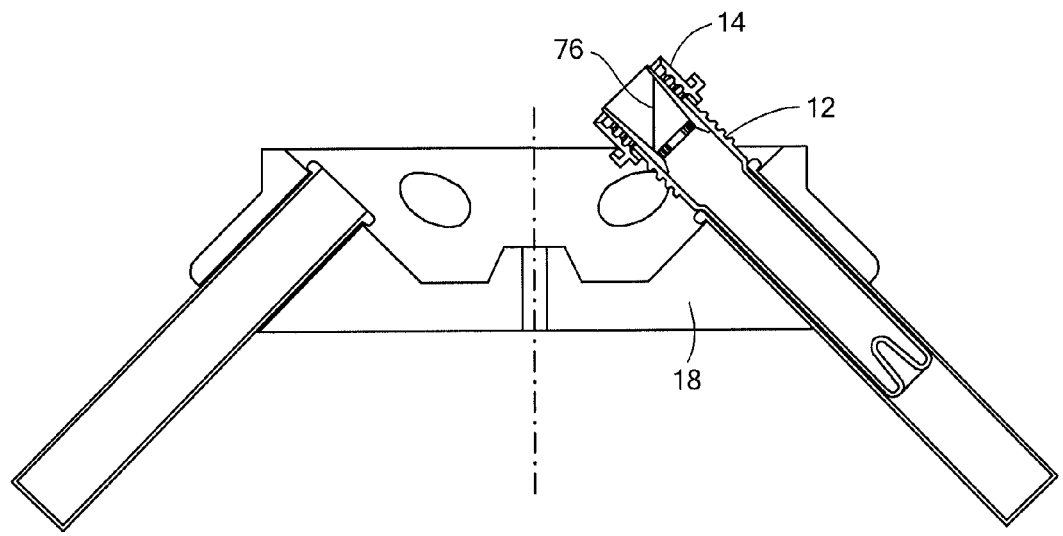
FIG. 7 is a cross-sectional view of a fixed angle type centrifuge rotor with a tube and cap of the present invention.
Figure 8:
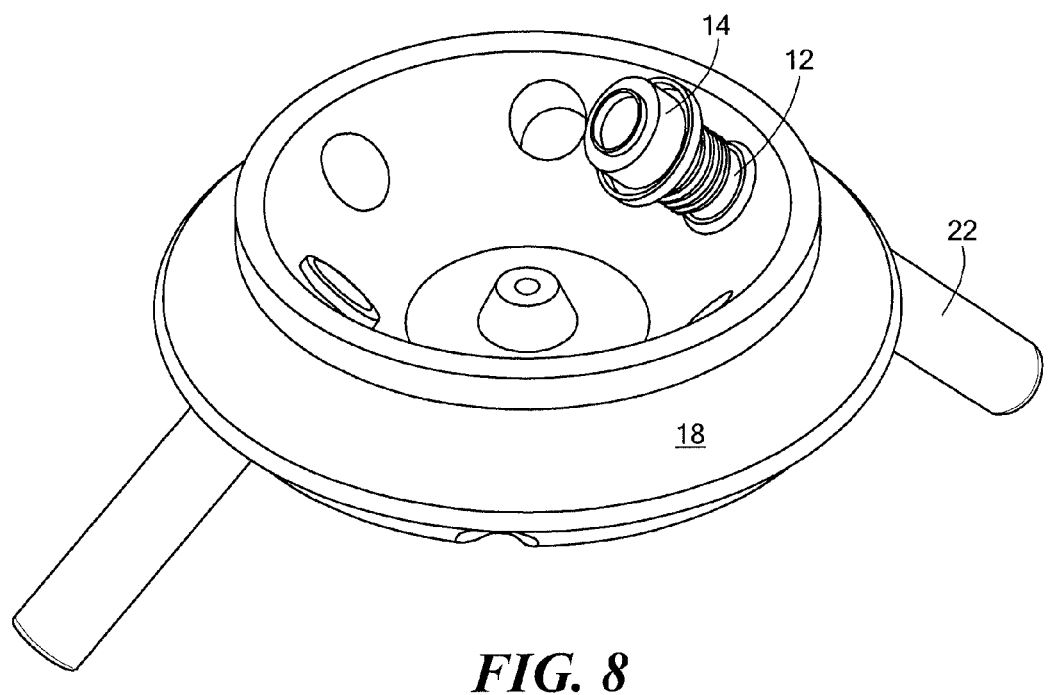
FIG. 8 is an isometric view of a fixed angle type centrifuge rotor with a tube and cap of the present invention.

A first embodiment of a centrifugal assembly for the separation of buoyant material is illustrated in FIGS. 1-6. The assembly includes a centrifuge tube 12, a meniscus-forming device such as cap 14, and a collector/mixer device 16. The collector/mixer device 16 is used to collect a fecal sample, place the sample in the tube, and mix the sample in the tube with a floatation fluid. The cap 14 attaches to the top of the tube for longitudinal or axial movement along the tube to create a meniscus, described further below. The tube can be inserted into a standard centrifuge 18, such as a swinging bucket type or a fixed angle type (FIGS. 7 and 8).

The centrifuge tube 12 is a cylindrical container, closed at a lower end 24 and open at an upper end 26. A mixing post 28 extends upwardly from the closed lower end inside the tube. The tube includes a cap engagement mechanism 30 at the open upper end 26. In the embodiment illustrated, the engagement mechanism is formed of external threads 64 that mate with internal threads 62 on the cap 14, allowing the cap to be rotationally raised or lowered along the axis of the tube. The tube can be formed of any suitable material, such as polystyrene, and is typically transparent to allow the contents to be viewed.

Figure 5:
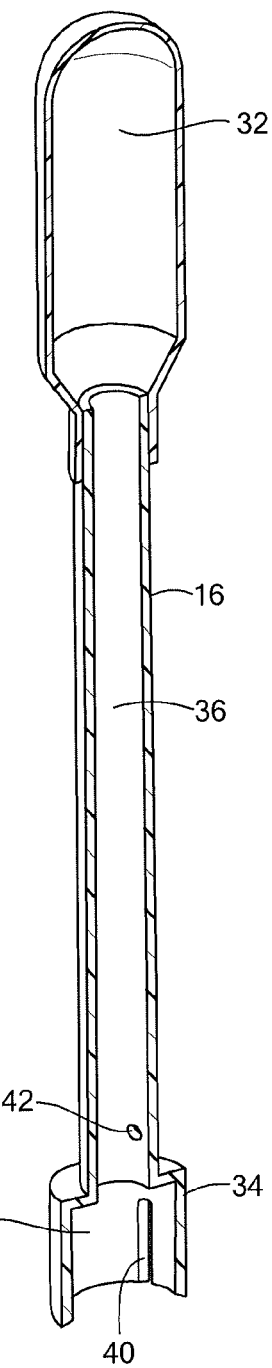
FIG. 5 is a cross-sectional isometric view of the collector/mixer device.

The collector/mixer device 16 includes a hollow squeezable member formed of a resilient material, such as a squeeze bulb 32 on one end. A coring chamber 34 is provided on the other end of the device. The bulb and the coring chamber are connected by a hollow, cylindrical stem 36. The coring chamber is a cylindrical cup 38 having slits 40 formed therein, which fits over the mixing post 28 in the tube. The slits can extend to the bottom edge of the cup (as shown in FIG. 5) or can terminate above the bottom edge (not shown). A user obtains a fecal sample by inserting the coring chamber into the fecal sample with a twisting motion. The device is then inserted into the tube 12 to which floatation fluid has been added. The user squeezes and releases the bulb 32 and rotates and/or reciprocates the coring assembly over the mixing post. The combined rotational/reciprocating action and fluid motion break up the sample and mix it with the floatation fluid. The slits 40 assist in mixing of the fecal sample with the floatation fluid in the tube. The collector/mixer also includes small diameter air vent holes 42 in the stem to allow release of air and facilitate the pumping of fluid when the bulb is squeezed and released. The collector/mixer device is removed and discarded once the fecal sample has been sufficiently broken up and mixed with the fluid.

In another embodiment (FIGS. 9 and 10), the collector/mixer device 16' is manufactured with a predetermined amount of floatation fluid 44 sealed within it. The seal can be formed by a disc or wafer 46 of a suitable material, such as a foil or plastic membrane, across the bottom of the stem. The seal is punctured by the mixing post 28' in the centrifuge tube 12' when the device with a fecal sample in the collection chamber is inserted into the tube, thereby releasing the fluid. This embodiment eliminates the need to prepare floatation fluid and the steps of measuring and pouring the fluid into the tube.

The collector/mixing device can be made in any suitable manner and from any suitable material, such as polyethylene or polypropylene. The device can be formed in one piece, for example, by blow molding. Alternatively, it could be formed in two or more pieces that are joined, for example, by adhesive, ultrasonic welding, or in some other manner.

Figure 3:
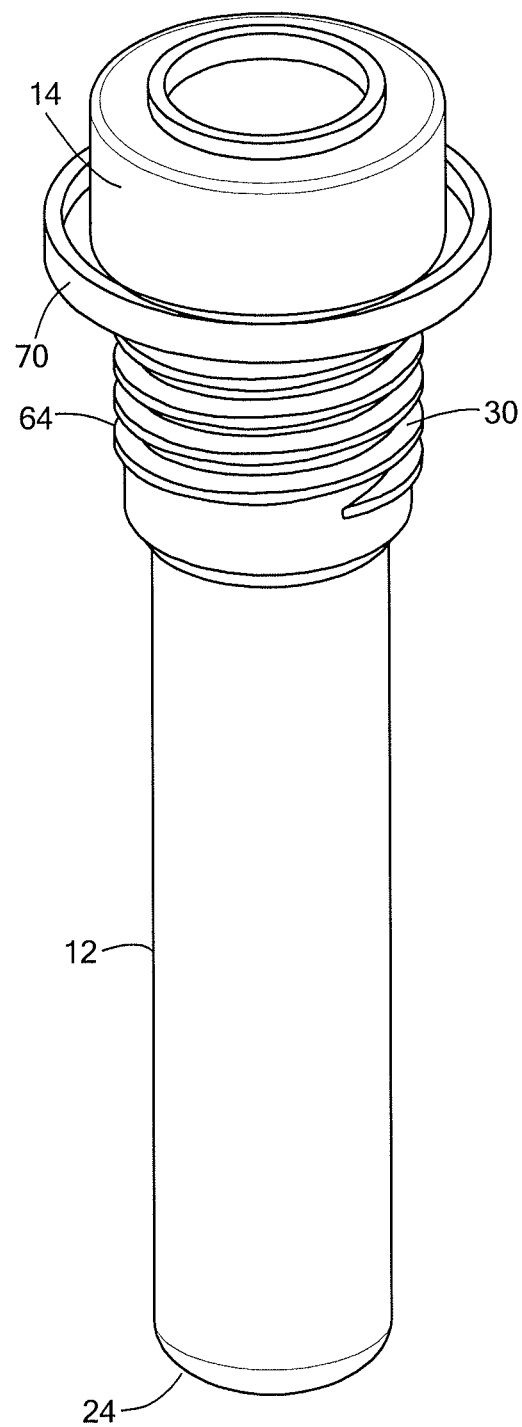
FIG. 3 is an isometric view of the tube of FIG. 1 along with a cap of the centrifugal assembly.
Figure 4:
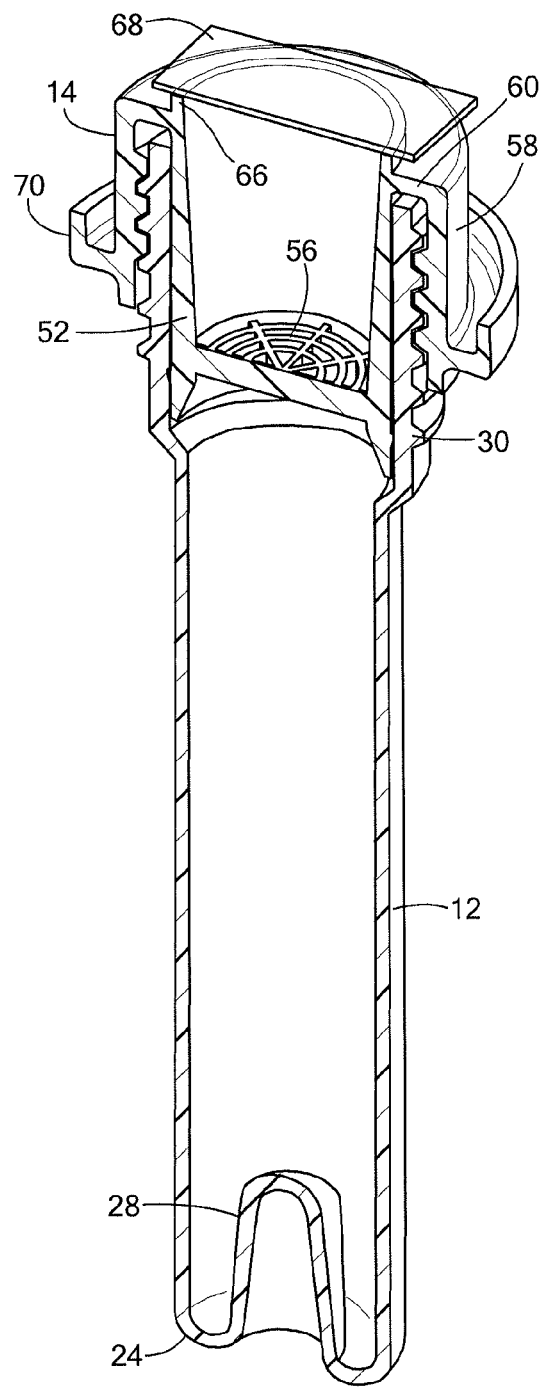
FIG. 4 is a cross-sectional isometric view of the tube and cap with coverslip.
Figure 6:
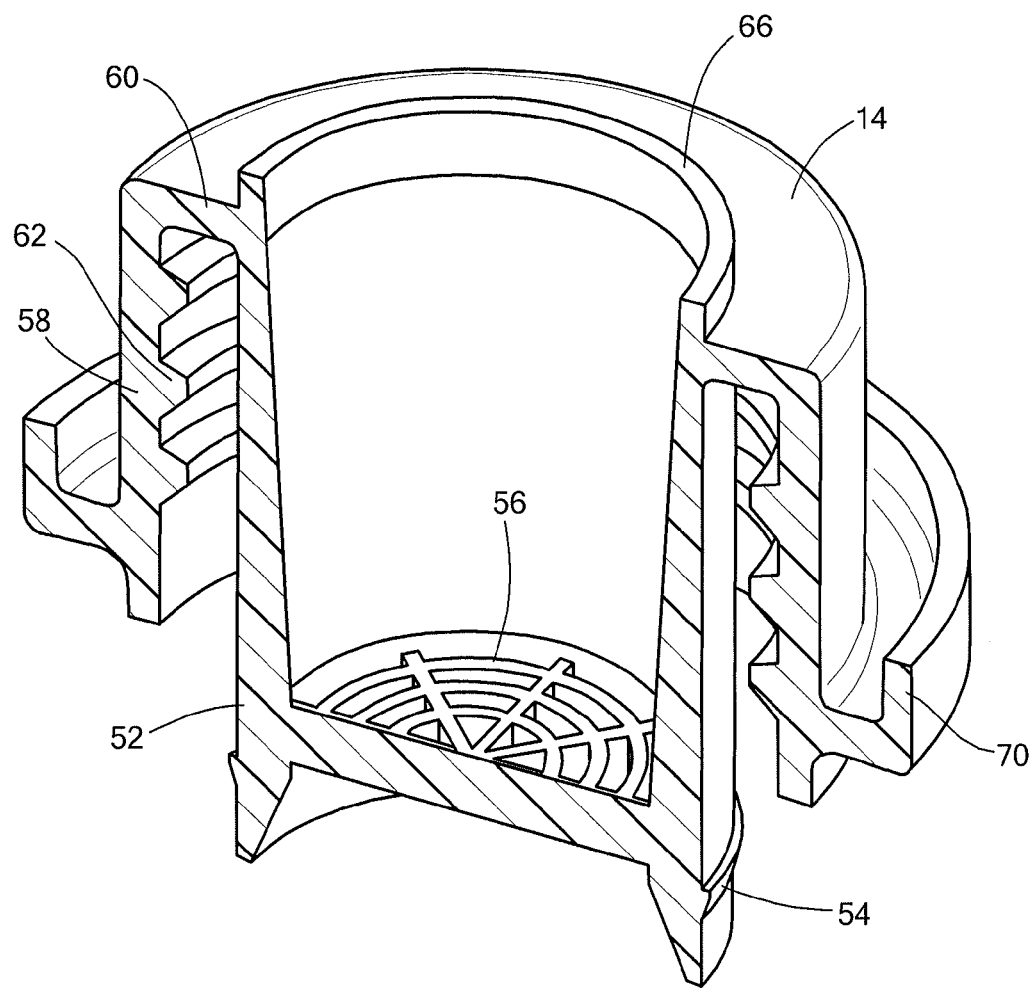
FIG. 6 is a cross-sectional view of the cap.

Referring to FIGS. 4 and 6, the cap 14 includes a depending sleeve 52, open at each end, that is sized to fit in sealing engagement inside the top of the tube 12. A seal element 54, such as a seal lip, is provided about an external surface of the sleeve to provide a fluid seal between the cap and the tube. A filter element 56 is formed across the bottom of the sleeve to prevent larger clumps of material from rising to the upper layers of the fluid. The filter openings are sufficiently large to allow ova to pass through to the surface during and after centrifugation.

An outer annular collar 58 is attached to the sleeve 52 by a flange 60 at the top of the cap. The collar is internally threaded with threads 62 to engage with the external threads 64 on the tube 12. The sleeve 52 extends above the flange 60 a small distance to form an annular upstanding ridge 66 on which a coverslip 68 (FIG. 4) can be placed. An overflow rim 70 extends around the outside of the annular collar 58 to catch any fluid that may spill over the top of the cap.

In use, the cap 14 is attached to the tube 12, after the fecal sample is added and sufficiently mixed, by screwing it on via the threads. Initially, the cap is not screwed fully down the tube, but is left in a predetermined raised position in which the top of the cap extends above the top of the tube. An optional locking tab 72 (FIG. 2) can be located on the tube to prevent the cap from being completely removed from the tube after use. Prior to centrifugation, additional floatation fluid can be added as needed to bring the fluid level above the filter 56 and below the top of the cap 14. A fill line may be provided on the tube or the cap to indicate to the user how much fluid to add. The tube and cap are placed in a centrifuge and spun, for example at 1500-2000×g for 5 minutes. Buoyant parasite ova move inwardly toward the center of rotation and travel toward the fluid surface. At the end of the spin cycle, the ova are concentrated in the upper layer 76 of fluid in the tube (FIG. 7). The tube is removed and placed in an upright position. The cap 14 is slowly rotated down the thread 64 and the submerged portion of the cap displaces the floatation fluid until the surface of the fluid rises to form a meniscus on the top of the tube at the coverslip ridge 66. In this manner, the fluid is raised without turbulence or mixing and consequently with minimal disturbance of the ova floating on the surface of the fluid. A coverslip 68 is placed on the ridge 66 in contact with the meniscus, and any spillage collects in the overflow rim 70. The assembly is allowed to stand for a short time, such as 2 minutes, to allow the maximum number of ova to settle near the fluid surface. The coverslip 68, with an accompanying layer of fluid containing ova, is then removed and placed on a microscope slide for standard microscopic analysis.

In an alternative embodiment (FIG. 11), the engagement mechanism 30" between the cap 14" and the tube 12" may include a detent 82 and a slot 84 that mate with a pin 86 protruding from the tube 12". When the pin engages the detent, the cap is maintained in the desired raised position for centrifugation. After the centrifugation step, the cap is raised slightly to move the pin 86 out of the detent 82 and then rotated until the pin moves into the slot 84, allowing the cap to be moved to the lower position.

In a still further embodiment (FIG. 12), the engagement mechanism 30''' includes a detent 82' and an angled slot 84' in the cap 14''' to form an engagement mechanism with a pin 86' on the tube 12". As with the embodiment of FIG. 11, when the pin fits within the detent, the cap is maintained in the raised position. To lower the cap, it is raised slightly to move the pin 86' out of the detent 82' and rotated until the pin moves into the slot 84', from where the cap can be further rotated and lowered to the lower position.

Figure 13:
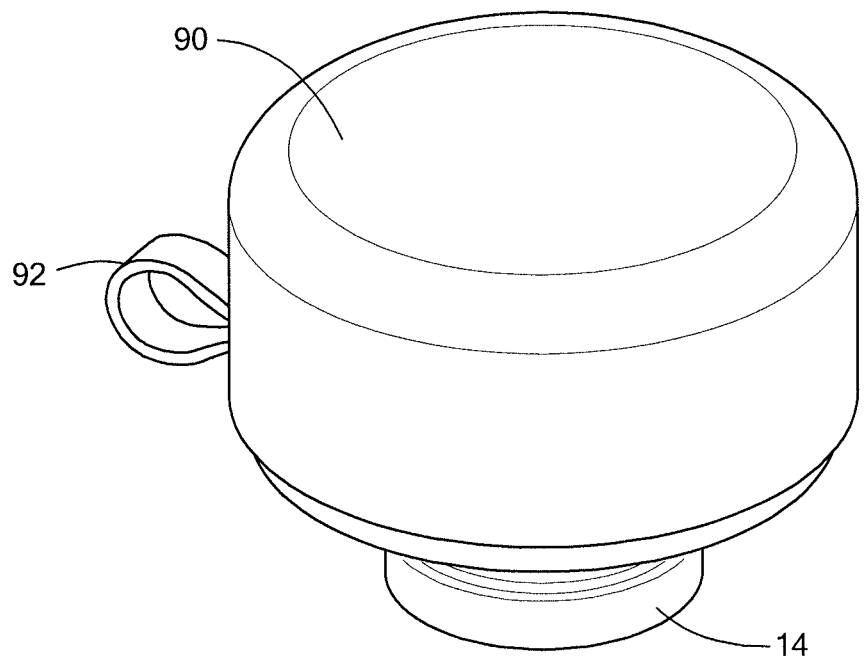
FIG. 13 is an isometric view of a cap with integral closure.
Figure 14:
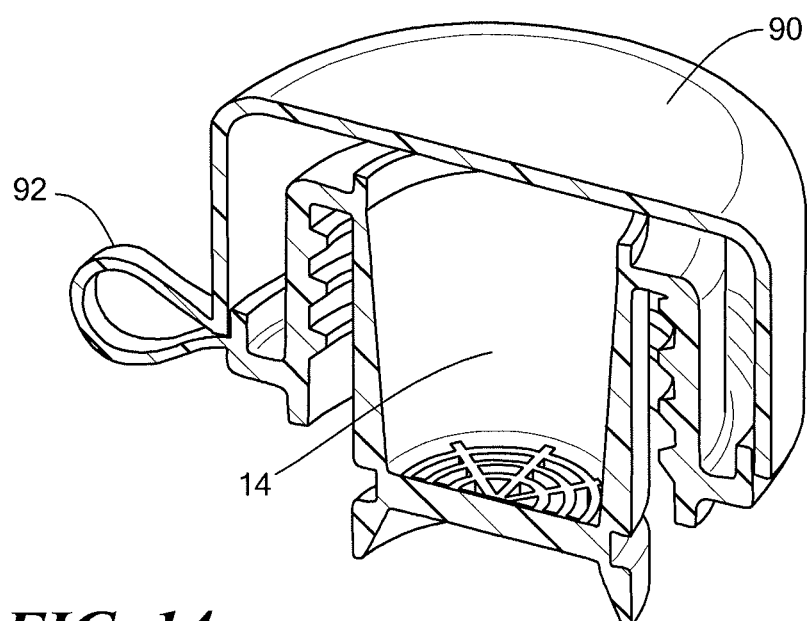
FIG. 14 is a cross-sectional view of the cap and closure of FIG. 13.

The cap 14 can also include a closure 90, illustrated in FIGS. 13 and 14. The closure can close the open upper end of the cap during centrifugation and for disposal of the entire assembly after use. The closure can be integrally formed with the cap, such as with a flexible or "living" hinge 92. The cap and closure can be formed in any suitable manner, such as by molding, of any suitable material, such as polyethylene or polypropylene.

A further embodiment is illustrated in FIGS. 15-18. The meniscus-forming device is an insert 114 that engages with an elongated tube 112 and is movable relative to the tube with respect to a long axis 113 of the tube. Any suitable engagement mechanism 116 can be provided to assist in the engagement while allowing the relative motion between the tube and the insert. For example, one or more external screw threads, partial threads, or thread tabs 118 on the insert 114 can be provided that mate with one or more internal screw threads or tracks 120 on an upper portion 122 of the tube 112 to guide rotation of the insert along the tube. The insert 114 is a hollow cylindrical element or sleeve 124 having an interior region 126 open at an upper end 128 and a lower end 130. An upper edge 132 forms a coverslip ridge 134. A filter element 136, such as a filter basket, is formed near the lower end 130 to aid in preventing clumps of larger material from rising to the top of the fluid within the tube and insert. The filter openings 138 are sufficiently large to allow ova in the fluid to pass through before and during centrifugation. A further embodiment of an insert 114' illustrates a filter element 136' in the form of a filter plate extending across the interior region 126' of the insert near the lower end 130' (see FIG. 18A). A seal element 140, such as an O-ring 142 disposed in an external annular recess 144 in the insert 114, is provided around the sleeve near the lower end 130 to provide a fluid seal with the tube 112. The seal element can take other forms, such as an integral lip (see lip 140' in FIG. 18A) or an O-ring overmolded in the insert 114.

In operation, after a fecal sample has been mixed with floatation fluid in the tube, the insert 114 is placed into the tube 112 in a raised position. The insert can be held in place in any suitable manner. For example, the thread tab 118 of the engagement mechanism of the insert can mate with a detent or cutout 146 on the tube (see aligned arrows 145, 147, and FIGS. 16 and 17). An additional suitable amount of fluid is added, which can be indicated by, for example, a fill line 143. After the centrifugation step, the insert is lowered by removing the tab 118 from the detent 146 and slowly rotating it down the tread or track 120 within the tube until the surface of the fluid forms a meniscus at the upper edge 132 of the insert. In this manner, the fluid surface is raised within the insert without turbulence or mixing and consequently with minimal disturbance of the ova at the upper layer of the fluid. Finger grips 148, such as vertical ribs 150, can be disposed at or near the upper end of the insert to aid the user in rotating the insert. A coverslip is placed on the ridge 134 in contact with the meniscus. The assembly is allowed to stand for a short time, such as 2 minutes, to allow the maximum number of ova to settle near the fluid surface. The coverslip, with an accompanying layer of fluid containing ova, is then removed and placed on a microscope slide for standard microscopic analysis.

Figure 21:
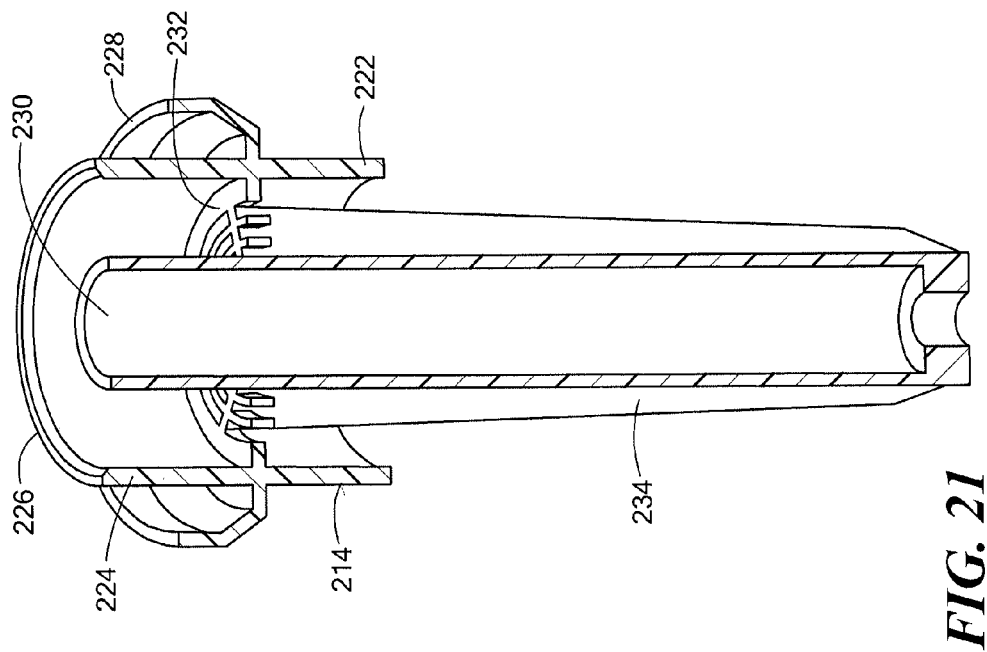
FIG. 21 is a cross-sectional view of the insert of FIG. 20.
Figure 20:
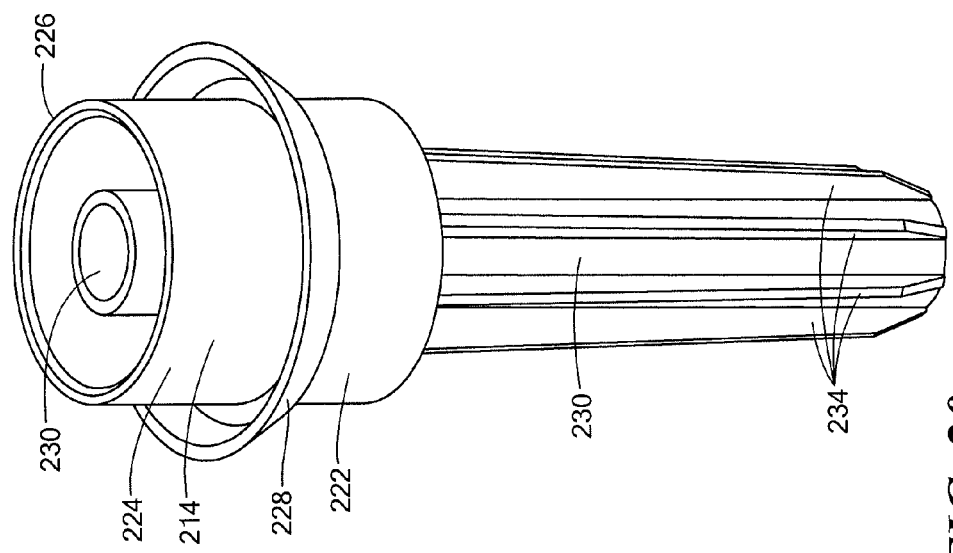
FIG. 20 is an isometric view of the insert of FIG. 19.

In a further embodiment (FIGS. 19-21), the centrifugal assembly includes a tube 212 and a meniscus-forming device such as tube insert 214. The collector/mixer device 16 with squeeze bulb described above or any other suitable collector/mixer device or method can be used with the tube of this embodiment to place and mix a fecal sample with floatation fluid in the tube.

The tube insert 214 fits within the tube 212 and remains during centrifugation. The insert includes an annular sealing flange 222 that fits over the outer diameter of the tube 212. In one alternative, the insert can snap into place in any suitable manner to provide a secure fit and prevent removal. A seal element, such as a bead or O-ring, can be provided about an internal surface of the flange 222 to assist in providing a fluid seal between the cap and the tube. An annular collar 224 extends upwardly from the sealing flange. A coverslip ridge 226, on which a coverslip can be placed, is formed at the upper edge of the collar. An overflow rim 228 extends around the collar to catch any fluid that may spill over the top of the coverslip ridge.

A fill conduit 230 is formed within the collar. As shown, the conduit is centrally located, coaxial with the collar and the tube. Elongated ribs or fins 234 are formed on the outer surface of the conduit. When the insert is placed in the tube, the fins displace fluid in the tube upwardly, toward the mouth of the tube, so only a minimal volume of fluid is contained in the upper half of the tube (for example, 1 ml of 5 ml total). This minimizes disturbance of the fluid, which enhances recovery of the ova.

The conduit 230 is connected to the flange 222 and the collar 224 by a filter element 232, such as a filter plate. The filter element aids in preventing clumps of larger material from rising to the top of the fluid. The filter openings are sufficiently large to allow ova to pass through to the surface before and during centrifugation. The conduit 230 is open at both ends 231, 233 to provide a passage for floatation fluid to be added to the tube after centrifugation to form a meniscus at the coverslip ridge 226. In this manner, the fluid is raised without turbulence or mixing and consequently with minimal disturbance of the ova floating on the surface of the fluid. The upper opening 231 of the conduit 230 is positioned slightly below the coverslip ridge 226, for example, by about 2 mm, to allow ova to freely collect along the underside of the coverslip after the meniscus is formed and the coverslip is placed atop the insert.

In operation, after a fecal sample is mixed with floatation fluid in the tube, the insert is inserted into the tube. Further floatation fluid may be added to raise the fluid to a desired level. A fill line may be provided on the tube to indicate to the user how much fluid to add. The device is placed into a centrifuge, such as a swinging bucket type or a fixed angle rotor. The centrifuge is spun, for example at 1500-2000×g for 5 minutes. Buoyant parasite ova move inwardly toward the center of rotation and travel toward the fluid surface. At the end of the spin cycle, the ova are concentrated in the upper layer of fluid surrounding the conduit 230 in the tube. The tube is removed and placed in an upright position. Floatation fluid is added through the conduit 230, which is at a level below that of the ova, so the ova in the upper layer of the fluid are not disturbed by the addition of the fluid. Fluid is added until a meniscus forms at the coverslip ridge 226. Spills are contained by the overflow rim 228 of the insert. A coverslip is placed onto the assembly, and the assembly is allowed to stand for a short time, such as 2 minutes, to allow the maximum number of ova to settle near the fluid surface. The coverslip with an accompanying layer of fluid containing ova is then removed and placed on a microscope slide for standard microscopic analysis.

Figures 22, 23:
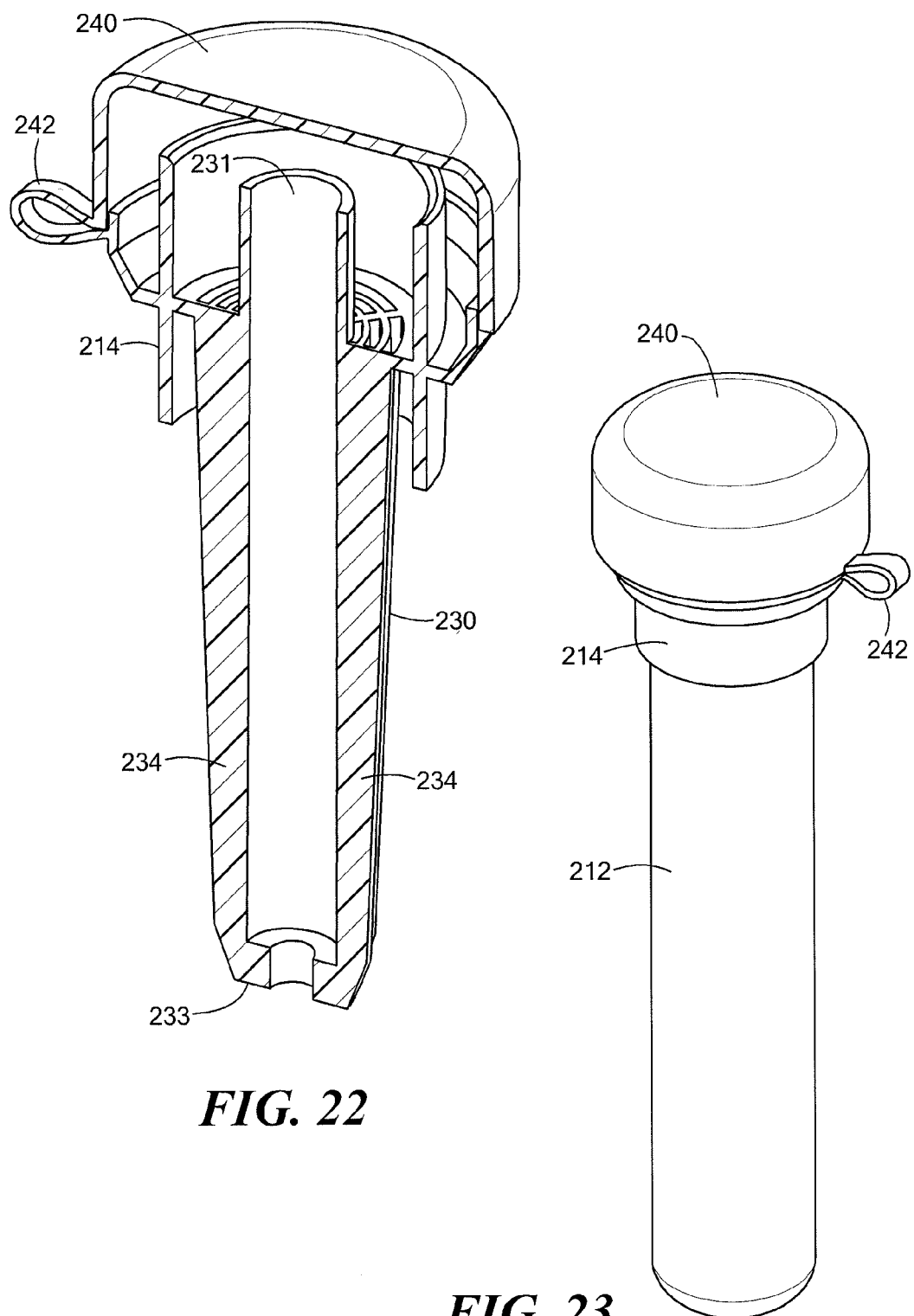
FIG. 22 is a cross-sectional view of the insert of FIG. 20 with integral closure.
FIG. 23 is an isometric view of the tube and insert of FIG. 19 with integral closure.

The insert 214 can also include a closure 240, illustrated in FIGS. 22 and 23. The closure can close the open upper end of the insert during centrifugation and for disposal of entire assembly. The closure can be integrally formed with the insert, such as with a flexible or "living" hinge 242. The insert and closure can be formed in any suitable manner, such as by molding, of any suitable material, such as polyethylene or polypropylene.

In another embodiment, an overflow rim in the form of a flanged opening 128' may be formed integrally with the centrifuge tube rather than on the insert. See FIG. 10. This overflow rim minimizes the chance that fecal material makes contact with the tube opening when sample material is added to the tube. In this embodiment, the insert irreversibly snaps into a groove at the underside of the tube flange.

In a still further embodiment, illustrated in FIGS. 24-29, the centrifugal assembly includes a centrifuge tube 312, a mixer insert 314, and a plunger 316 cooperative with the mixer insert. The mixer insert 314 is used to collect a fecal sample and place the sample in the tube. To mix the sample in the tube with a floatation fluid, the plunger 316 reciprocates axially within the mixer insert and attaches to the mixer insert to rotate the insert within the tube. The mixer insert remains in the tube during and after centrifugation. The plunger is removed after mixing and prior to centrifugation.

The mixer insert 314 is a hollow, cylindrical member having a diameter less than the inner diameter of the centrifuge tube. Two or more ribs 322 may be provided on the outer surface of the mixer insert to stiffen the insert and center the insert within the tube. A coring chamber 324 is formed on the lower end of the cylindrical member. The coring chamber is a cylindrical cup 326 having slits 328 formed therein, which fits over a mixing post in the bottom of the tube. The top of the coring chamber is formed by a plate 330 having fluid openings 332 therein to allow the floatation fluid to flow therethrough to assist mixing of the sample when the plunger is reciprocated within the insert. (See FIG. 28.) The slits 328 in the coring chamber allow the fecal material to pass through during mixing. A filter element 336, such as a plurality of filter fins, is formed around the top of the cylindrical member of the mixer insert. The filter fins prevent larger clumps of material from rising to the upper layers of the fluid while allowing ova to pass through to the fluid surface before and during centrifugation.

The plunger 316 is formed from an elongated member 340 that fits within the interior of the cylindrical member of the mixer insert. In the embodiment illustrated, the member has a cross or X shape in cross-section. A plate 342 on the bottom of the elongated member displaces fluid when the plunger is reciprocated to aid in mixing. A handle 344, such as a button or knob, is located on an upper end for a user to grasp for reciprocating and rotating the plunger. The mixer insert 314 includes a keying slot 346 in which the elongated member 340 fits to allow the mixer insert to rotate with the plunger to further assist in mixing. (See FIGS. 27, 29.) Other keying mechanisms between the plunger and mixer insert can be provided. The plunger is removed and discarded once the fecal sample has been sufficiently broken up and mixed with the fluid.

The centrifugal tube 312 includes a retaining tab 348 to latch the mixer insert into the tube (FIG. 29). A fill port 350 is formed on a side of the tube. The fill port has an opening below the level of the filter element 336 of the mixer insert in the tube. After centrifugation, floatation fluid is added through the fill port to raise the level of fluid in the tube to form a meniscus at the top of the tube.

In operation, the user obtains a fecal sample in the coring chamber 324 of the mixer insert 314. Fluid is added to the tube, and the insert is placed in the tube. The plunger 316 is inserted into the insert 314, and rotated, with the insert attached, and reciprocated to break up the sample and mix it with the fluid. The plunger is then removed and discarded. Additional fluid may be added to the tube if necessary to bring the fluid level above the filter element 336 and below the top of the tube. A fill line may be provided on the tube to indicate to the user how much fluid to add. The tube, with the insert, is placed in a centrifuge and spun, for example at 1500-2000×g for 5 minutes. Buoyant parasite ova move inwardly toward the center of rotation and travel toward the fluid surface. At the end of the spin cycle, the ova are concentrated in the upper layer of fluid. Floatation fluid is added through the fill port 350 at a level below that of the ova, so the ova in the upper layer of the fluid are not disturbed by the addition of the fluid. Fluid is added until a meniscus forms at the top of the tube. A coverslip is placed onto the assembly, and the assembly is allowed to stand for a short time, such as 2 minutes, to allow the maximum number of ova to settle near the fluid surface. The coverslip with an accompanying layer of fluid containing ova is then removed and placed on a microscope slide for standard microscopic analysis.

The invention is not to be limited by what has been particularly shown and described, except as indicated by the appended claims.

What is claimed is:

1. A centrifugal assembly for separation of buoyant material, comprising:
   a tube configured for containing a floatation fluid and a sample of matter to be separated, wherein the tube is elongated with respect to an axis and includes an open upper end and a closed lower end; and
   a meniscus-forming device engageable with and movable along the tube with respect to the axis, the device comprising an insert configured for sealing engagement with an interior surface of the tube, the insert including a sleeve depending within the tube and defining an interior region, the insert further including an open upper end disposed above the upper end of the tube at which a meniscus is formable, the sleeve having a volume sized to displace a volume of the floatation fluid in the tube upwardly to form a meniscus at the open upper end of the insert when the insert is moved a distance downwardly along the tube, and a filter element disposed to prevent passage of material of a size greater than openings in the filter element into at least a portion of the interior region of the sleeve.

2. The assembly of claim 1, further comprising an engagement mechanism on the tube to mate with the meniscus-forming device to retain the meniscus-forming device at a raised position and to allow the meniscus-forming device to be lowered with respect to the axis of the tube to a position that allows a meniscus to form at the open upper end.

3. The assembly of claim 2, wherein the engagement mechanism comprises a thread formed on an internal surface of the tube, and the meniscus-forming device includes at least a partial thread on an external surface of the insert matable with the thread on the tube, and the tube further includes a detent matable with the partial thread when the meniscus-forming device is in the raised position.

4. The assembly of claim 2, wherein the engagement mechanism comprises a thread formed on an external surface of the tube, and the meniscus-forming device includes a collar extending externally of the tube and a thread on the collar matable with the thread on the tube.

5. The assembly of claim 2, wherein the engagement mechanism comprises a pin extending from an external surface of the tube, and the meniscus-forming device includes a collar extending externally of the tube and a detent matable with the pin when the meniscus-forming device is in the raised position, and the meniscus-forming device further includes a slot matable with the pin to allow the meniscus-forming device to move axially along the tube.

6. The assembly of claim 5, wherein the slot is angled with respect to a tube axis.

7. The assembly of claim 5, wherein the slot is axially aligned with the axis of the tube.

8. The assembly of claim 1, wherein the meniscus-forming device includes a collar extending externally of the tube and an overflow rim formed circumferentially around the collar.

9. The assembly of claim 1, wherein a ridge is formed around the open upper end to support a coverslip.

10. The assembly of claim 1, wherein the meniscus-forming device includes an integrally attached cover.

11. The assembly of claim 1, wherein the tube includes a latching mechanism to retain the meniscus-forming device.

12. The assembly of claim 1, wherein the filter element comprises a filter plate extending across the interior of the sleeve at or near the lower end of the sleeve.

13. The assembly of claim 1, wherein the filter element comprises a filter basket depending from the lower end of the sleeve.

14. The assembly of claim 1, further comprising a collector/mixer device comprising a coring chamber, a squeezable member, and a hollow stem connecting the coring chamber and the squeezable member to allow fluid flow to and from the coring chamber upon squeezing of the squeezable member, the collector/mixer device configured to fit within the tube, the coring chamber configured to fit over a mixing post at the bottom of the tube, when the meniscus-forming device is not engaged with the tube.

\* \* \* \* \*